United States Patent
Gaither et al.

(10) Patent No.: US 6,408,702 B1
(45) Date of Patent: Jun. 25, 2002

(54) WOOD PROCESSING DRIER SENSOR

(75) Inventors: Lum C. Gaither; Wesley Harbour, both of Hot Springs, AR (US)

(73) Assignee: Automated Control Engineering Inc., Hot Springs, AR (US)

( * ) Notice: Subject to any disclaimer, the term of this patent is extended or adjusted under 35 U.S.C. 154(b) by 0 days.

(21) Appl. No.: 09/323,216

(22) Filed: Jun. 1, 1999

(51) Int. Cl.[7] .................................................. G01N 1/00
(52) U.S. Cl. .................................................... 73/864.81
(58) Field of Search ........................ 73/863.51, 863.56, 73/863.57, 863.83, 863.84, 864.81, 29.04; 162/49

(56) References Cited

U.S. PATENT DOCUMENTS

| | | | |
|---|---|---|---|
| 3,595,087 A | 7/1971 | Starks | 73/422 R |
| 4,055,088 A | 10/1977 | Diss | 73/424 |
| 4,056,983 A | 11/1977 | Mazzetti | 73/423 R |
| 4,156,507 A | 5/1979 | Gokabowski et al. | 241/75 |
| 4,562,747 A | 1/1986 | Jaeger | 73/863.54 |
| 4,574,645 A | 3/1986 | Allen et al. | 73/863.51 |
| 4,896,795 A | 1/1990 | Ediger et al. | 222/63 |
| 4,918,999 A | 4/1990 | Wenshan et al. | 73/863.54 |
| 4,993,273 A | 2/1991 | Temler | 73/864.32 |
| 5,101,672 A * | 4/1992 | Anthony et al. | 73/864.81 |
| 5,129,267 A * | 7/1992 | Nicholls | 73/863.84 |
| 5,604,996 A | 2/1997 | Bestwick et al. | 34/484 |

* cited by examiner

Primary Examiner—Robert Raevis
(74) Attorney, Agent, or Firm—Stephen D. Carver

(57) ABSTRACT

A particle sampling system reads the moisture content of particulates (i.e., wood flakes) travelling through a pneumatically-driven conduit to control the remote drier. A rotatable hood penetrating an opening in the conduit is secured by a suitable mounting flange. When the hood is aimed upstream, facing the particle flow, a captivated sample drops through the apparatus into a special sampling compartment. After a reading the hood is rotated into a position facing downstream. Moisture-reading apparatus transmits light through the sampling window to determine moisture content. Readings may be relayed back to the drier for operating parameter correction. A suitable drive motor activates the hood assembly through a friction drive ring. A valve plate within a special housing may be switched between a closed position, defining the sampling compartment within its enclosure, and an open position, venting the apparatus to atmosphere. When the hood faces downstream, the valve plate is opened, and the sample is suctioned back into the particulate stream within the conduit to recycle raw materials. After the sample is returned, the valve closes and the hood is rotated back into a sampling position, enabling the cycle to repeat.

16 Claims, 11 Drawing Sheets

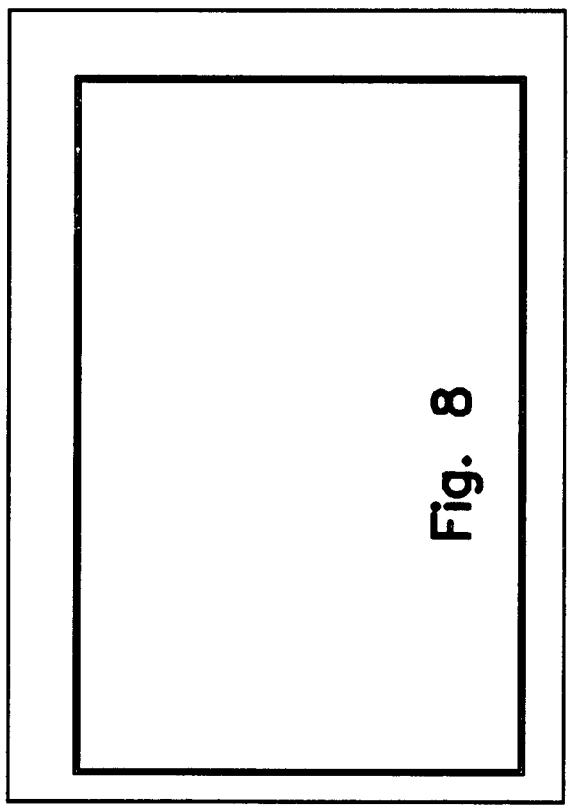
Fig. 8
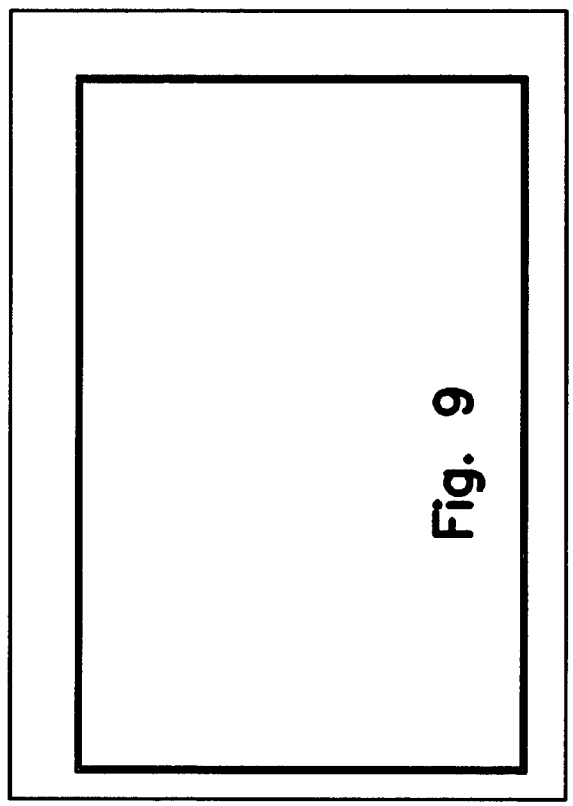
Fig. 9
Fig. 10

WOOD PROCESSING DRIER SENSOR

BACKGROUND OF THE INVENTION

I. Field of the Invention

Our invention relates generally to devices for sampling and testing particulate matter, including materials such as wood flakes and the like. More particularly, this invention relates to product monitoring devices characterized by remote, rotatable heads disposed within a product conveying chute that may be moved towards or away from the direction of particulate flow to captivate a sample. Known prior art relative to our invention is seen in Class 73, Subclasses 863.51, 863. 52, and 863.56.

II. Description of the Prior Art

A variety of contemporary wood products such as oriented strand boards and laminates are formulated from wood flakes and particles. These flakes are manufactured on site from billets or tree length wood. Raw wood chips are shipped in bulk to various manufacturing installations. The large, fungible mass of chips arriving at the manufacturing facility is of inconsistent density and moisture content. For quality control purposes a uniform mixture is desirable. One or more drying and mixing stages are commonplace.

A typical manufacturing process may pneumatically transport raw wood flakes from the critical drying stage to various downstream process stages. Between the process stages, flakes are sucked through a large pipe. It has been previously recognized by those skilled in the art that product quality may be better controlled if consistency in moisture content is achieved. The ability to sample the wood flakes immediately behind the drying process and check the moisture content allows the drying operations to be more closely controlled. Moisture readings of critical samples derived downstream may be employed to derive critical dryer control signals used to modify manufacturing parameters upstream. These readings can be used, for example, to speed up or slow down the flow of wood flakes through the drier. Where for example, oriented strand board is being manufactured; the flake moisture content must be tightly regulated. If the incoming flakes are over-dried, too much glue will be used. If the flakes are too moist, too little glue will be used. This can seriously affect the delamination of the finished product.

Prior art sampling devices collected wood flakes travelling within a pipe or conduit with a fixed, inlet end. Often design limitations inherent in prior art fixed sampling ends made it difficult for the monitored product to be sampled properly. The particulate mass flowing through a typical wood flake delivery pipe, for example, comprises a variety of wood particles of different sizes and moisture.

The wood drying in these inline processes has been largely uncontrollable because moisture reading of the end products was not obtainable for several minutes behind the drying operation.

A negative pressure blow pipe system is used for conveying the wood particles through the rotary drum drying operation in the process and the ability to sample the dried flakes immediately behind the dryer is a large step in better controlling the drying operation.

Because the typical granular mixture involves so many wood chips of different sizes and shapes, it has proven difficult to obtain a statistically representative sample that can be properly analyzed for process control. Usually fixed sample tubes obtain a more representative sample if they are mounted close to the pipe inlet. However, it is often cumbersome and inconvenient to mechanically mount the complex sampling apparatus immediately proximate an inlet. It is much more practicable to mount the sampling apparatus midstream, in an area that is easily and safely accessible to workman and equipment.

U.S. Pat. Nos.3,595,087 and 4,574,645 are the closest prior art references known to us. These patents show sampling mechanisms secured to transfer conduits. The samplers comprise rotatable hoods positioned within the flow path. Samples are captured, measured, and then discarded. The hoods may be rotated between a first operative position disposed directly within the flow path for capturing samples, and a second operative position disposed 180 degrees in the opposite direction. However, said devices do not perform the moisture determination; samples must be manually removed for testing at a remote location. Furthermore, samples are not automatically returned to the airstream after testing. While these systems are improvements over other more cumbersome designs, they tend to be slow, and corrective information needed for feedback to the remote drier cannot be derived and monitored in real time.

SUMMARY OF THE INVENTION

This invention provides a real time sampling and sensing system for monitoring characteristics (i.e., moisture content) of particulates (i.e., wood flakes.) The system comprises a sensor having a rotatable head thrust within the flow path of the particulate-laden airstream. When the rotary head is turned to face the flow of wood material, a sample is captured, and stored temporarily within a lower sensing chamber. The rotary head may then be returned to the downstream-facing position. Immediately afterwards the captivated sample may be "sensed" to determine moisture content, The wood flakes captivated within the lower part of the sensing chamber are held against a glass port, and an adjacent moisture meter reads the moisture. Afterwards, the valve in the lower section of the device is opened. Since the conveying system is operating under negative pressure (less than atmospheric) the sample is swept back into the material flow by the inrush of air.

The electrical information can be relayed to control circuitry to be processed into adequate control signals for feedback to the remote drier. In other words, corrective feedback signals may be generated virtually instantaneously with the capture of a particle sample, minimizing delays and errors.

Once the sample is discharged the damper shuts and the unit waits until an another capture signal is received. In response to such a signal, another sample is captured, read, and then returned to the conduit; in other words, the entire operation is repeated. Real time corrective parameters can thus be electronically produced concurrently with drier operation.

Thus a general object of our invention is to provide a dynamic sampling device for monitoring a stream of particulates.

More particularly, it is an object to provide a highly reliable monitoring system for sampling wood flakes traveling through a negative pressure pneumatic pipe.

Another basic object is to precisely control the moisture of wood flakes traveling through a manufacturing process.

Yet another object is to provide a dynamic sampling process of the character described that provides sufficient moisture feedback data downstream of a process to provide feedback and control signals used for adjusting and controlling an upstream process.

A related object is to automatically sample particulate materials as they are pneumatically transported, and to concurrently derive real time corrective parameters for feedback to the remote drier.

A basic object is to sample particulate matter, i.e., wood flakes, flowing through a negative pressure pipe with a minimum of product waste.

A related object of the present invention is to provide an improved moisture sample for wood flakes.

Also, it is an object to provide a moisture sampling and control system of character described that is ideally adapted to handle samples of particulate materials that vary widely in moisture content, size and shape.

Another important object is to provide a wood particle sampling system of the character described that returns samples, after deriving a reading, to the pneumatic pipe, thereby minimizing waste.

Yet another object is to provide a sampling device that may automatically and remotely be switched between product collecting and neutral positions.

These and other objects and advantages of the present invention, along with features of novelty appurtenant thereto, will appear or become apparent in the course of the following descriptive sections.

BRIEF DESCRIPTION OF THE DRAWING

In the following drawings, which form a part of the specification and which are to be construed in conjunction therewith, and in which like reference numerals have been employed throughout wherever possible to indicate like parts in the various views:

FIG. 10 is a diagrammatic view showing how to orient FIGS. 8 and 9 for viewing; and, FIG. 11 is a block diagram of the preferred electrical control system.

DETAILED DESCRIPTION

Figure 1:
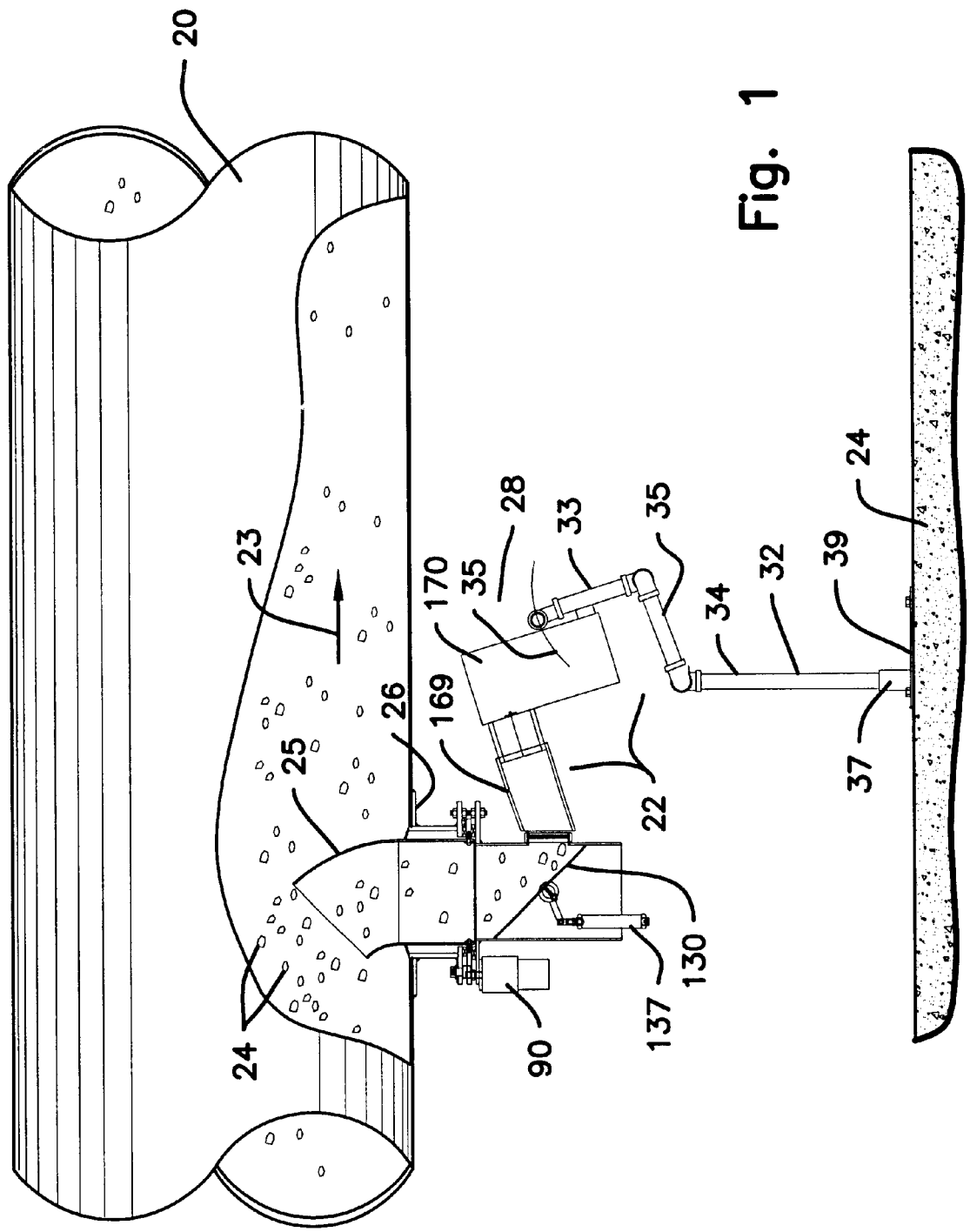
FIG. 1 is a fragmentary, pictorial view showing a portion of an inclined, pneumatic pipe for transporting wood flakes, with the instant wood drying system installed, with the rotary head facing upstream (i.e., oriented in a particle-captivating position) to obtain wood-flake sample, and slowing the butterfly valve closed.
Figure 2:
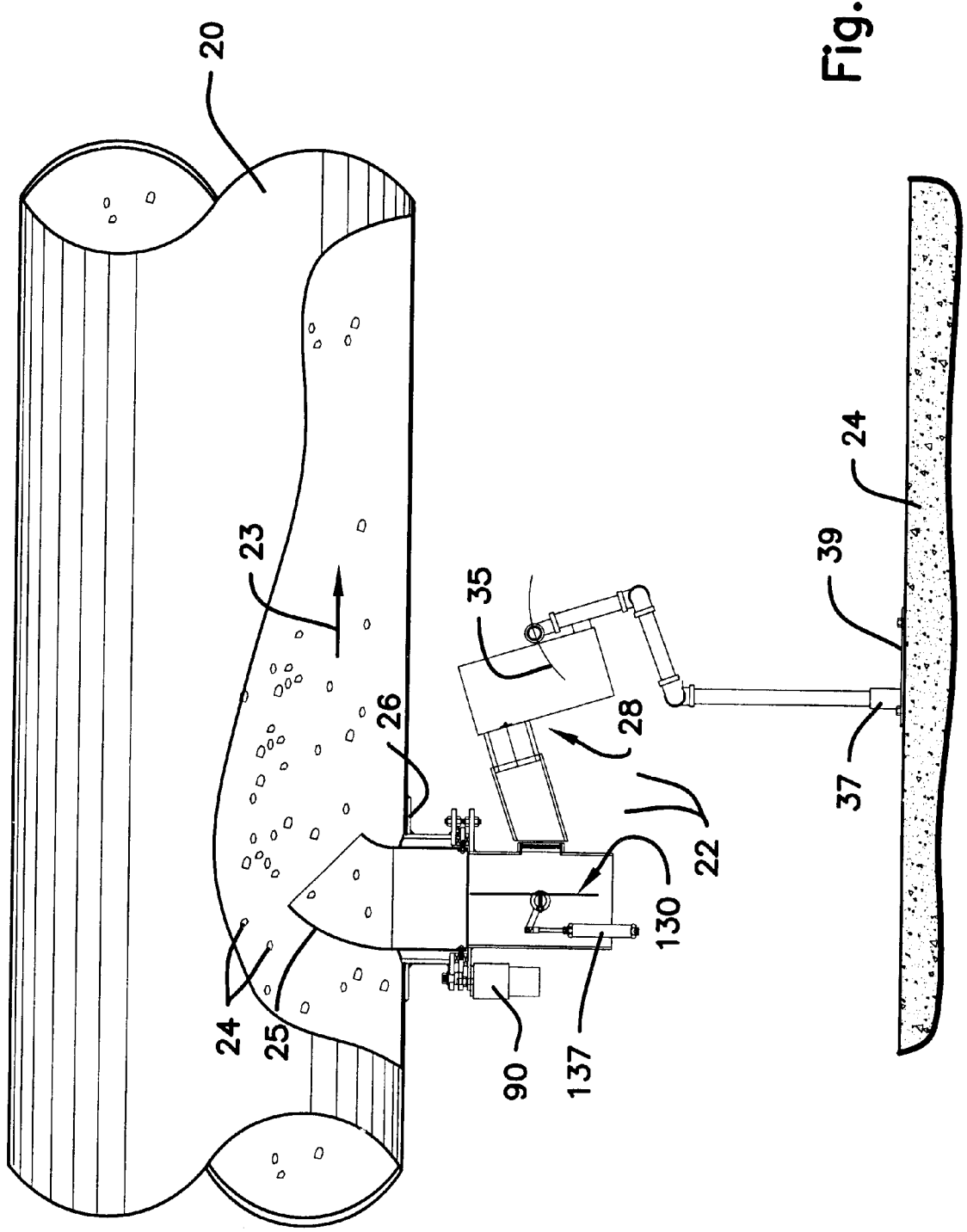
FIG. 2 is a fragmentary, pictorial view similar to FIG. 1, but showing the head rotated to a particle-discharging position facing downstream to return a sample to the particle stream, with the butterfly valve open.

With initial reference directed to FIGS. 1 and 2 of the appended drawings, a typical forced flow conduit that conducts wood particles or flakes has been generally designated by the reference numeral 20. The pressure within conduit 20 is less than atmospheric. The preferred drying process sampler apparatus has been designated by the reference numeral 22. The rotatable hood apparatus 25 to be described later is secured within a precut opening in the conduit 20 by a flange 26. When oriented as in FIG. 1, hood 25 captures particles 24 to obtain a sample for moisture evaluation. When rotated to the position of FIG. 2, hood 25 releases and returns previously captured particles into the airstream.

The moisture reading apparatus, generally designated by the reference numeral 28, should be structurally supported adjacent conduit 20 near head 25. The illustrated pipe framework 32 amply supports the moisture sensor above a stable, preferably concrete pad 24. Stanchion 34 rises from a sleeve-like, screwed coupling 37 that is rigidly attached to a rigid, rectangular baseplate 39 secured to the concrete platform 24. The schedule-forty screwed pipe members 33, 34 and elbows 38 may be manipulated as necessary to position the apparatus, which may be moved in several arcs such as arc 35. A vigorous particle stream or airflow designated by arrow 23 is established within conduit 20. This particle stream comprises numerous wood flakes 24 dynamically travelling from left to right (i.e., as viewed in FIGS. 1 and 2) through conduit 20 between manufacturing stages of a typical wood-chip process.

With joint reference now directed to FIGS. 3 and 6–8, the rotatable hood apparatus 25 comprises a stainless steel elbow 60. The open end 65 of the elbow forms a spout providing a pathway for sampled particulates —it can rotated into or out of the airstream within the conduit 20. The opposite end of the elbow 60 is concentrically welded at seam 61 to a pipe 62. Elbow 60 and pipe 62 are eight inches in diameter in the best mode known at this time. Pipe 62 terminates at its lower base in a rigid, friction drive ring 63. The annular friction ring 63 is concentrically secured to pipe 62 with a plurality of fasteners 64 that are of radially, spaced-apart about the interior of pipe 62. The centers of pipe 62 and ring 63 coincide with the longitudinal axis of the hood assembly.

Flange 26 is secured to the outside of conduit 20 concentrically about an access opening that is cut by standard techniques. An elongated, external pipe 66 welded to mounting flange 26 concentrically shrouds pipe 62. Pipe 66 rigidly extends from mounting flange 26 on the conduit 20 to a concentric, annular plate 68 to which it is also welded. Pipe 66 is ten inches in diameter in the best mode. The annular support plate 68 also concentrically surrounds pipe 62. It rigidly supports a larger, spaced-apart, and substantially circular ring-shaped plate 72 that has a rectangular opening 75 (FIG. 8) that admits valve housing 76 (FIGS. 3, 9) to be described hereinafter. Plate 72 that is secured by a plurality of radially, spaced-apart fasteners 77 (FIGS. 5, 6, 8) comprising elongated, threaded rods 78 extending between suitable orifices 81 (FIG. 8) in plates 68, 72 that are compressed in place by a plurality of threaded hex-nuts 79.

Figure 4:
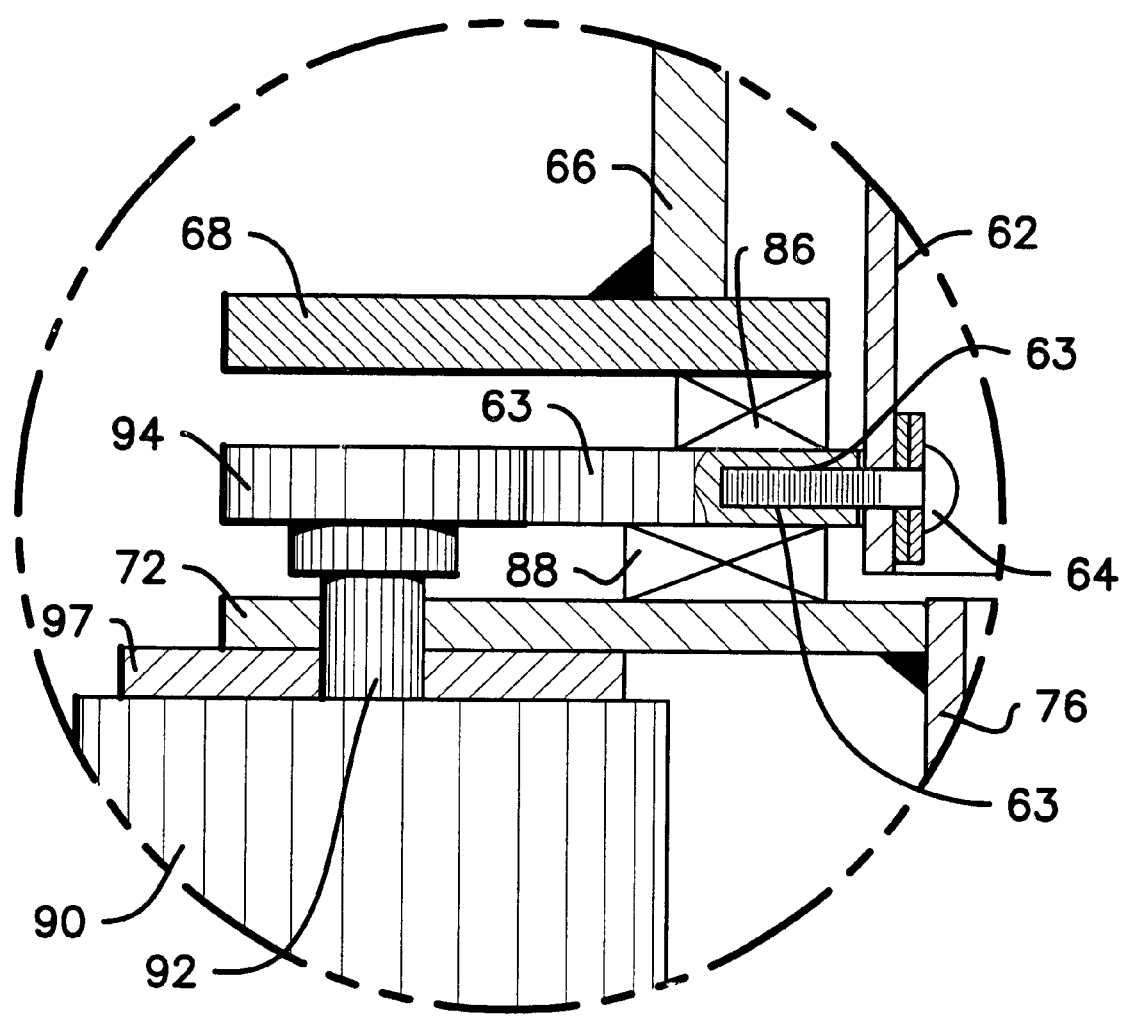
FIG. 4 is an enlarged, fragmentary sectional view of circled region 4 in FIG. 3, showing the motor drive arrangement.
Figure 5:
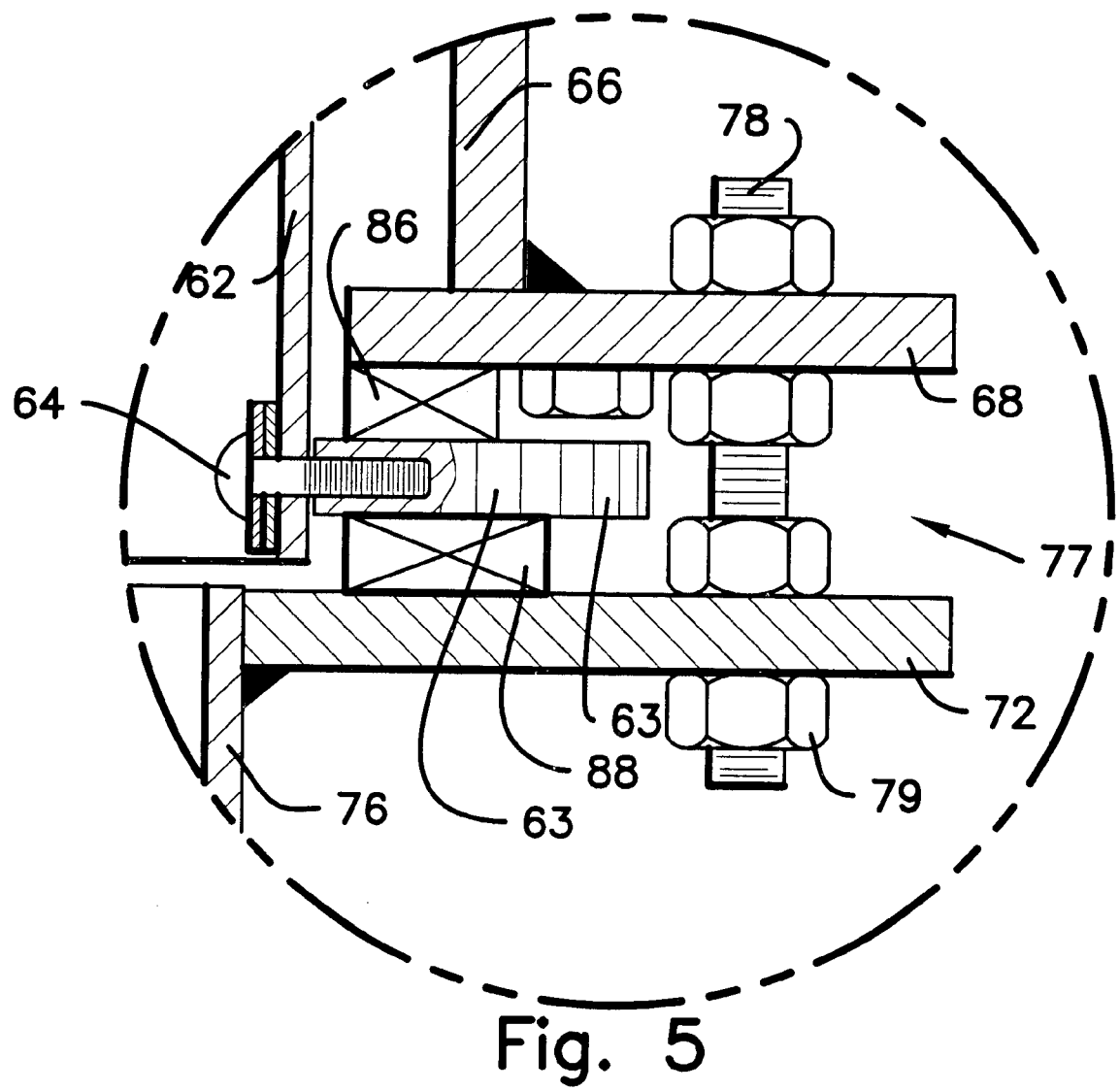
FIG. 5 is an enlarged, fragmentary sectional view of circled region 5 in FIG. 3.
Figure 6:
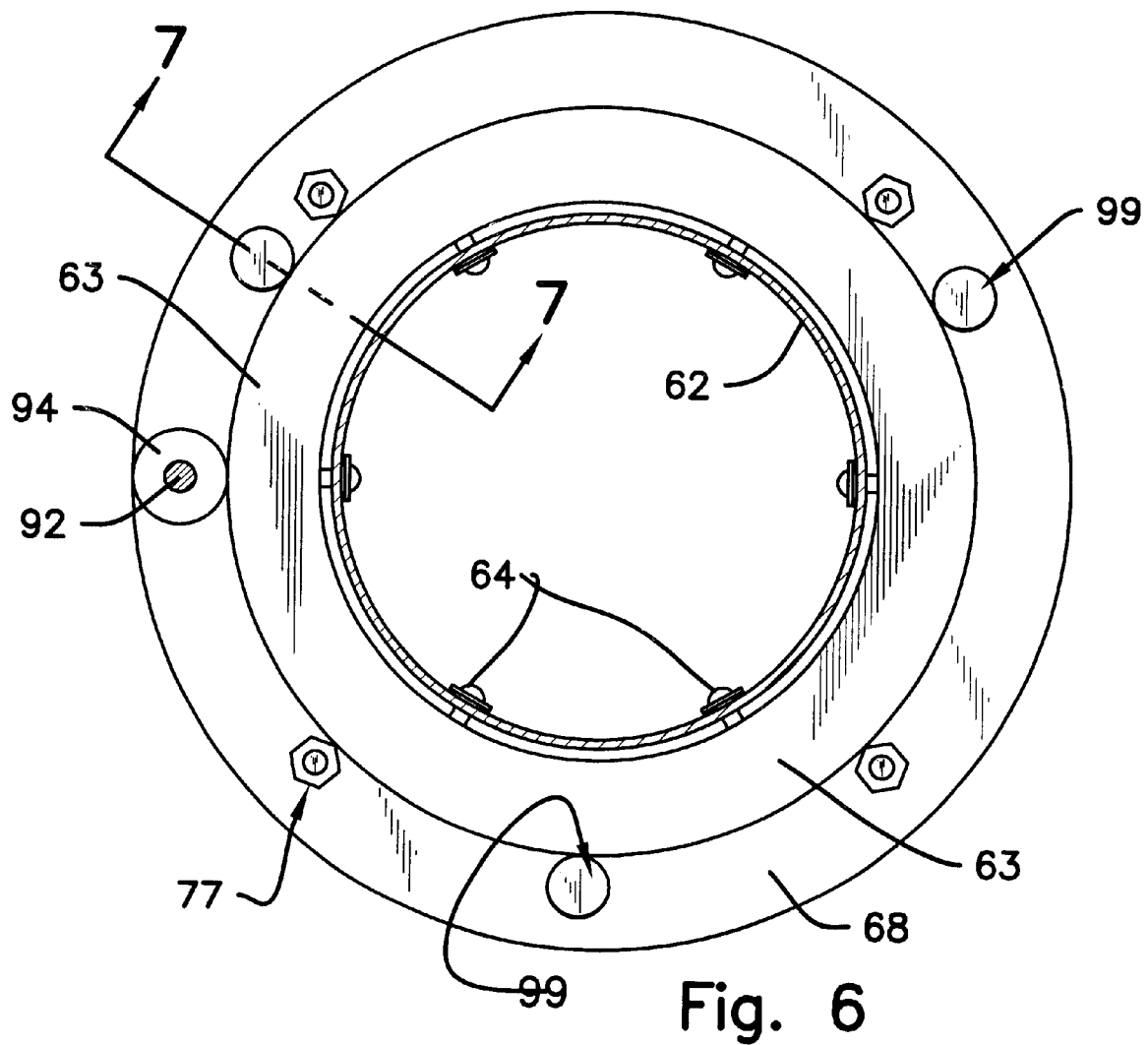
FIG. 6 is a fragmentary, sectional view taken generally along line 6—6 in FIG. 3, with portions omitted for clarity.
Figure 7:
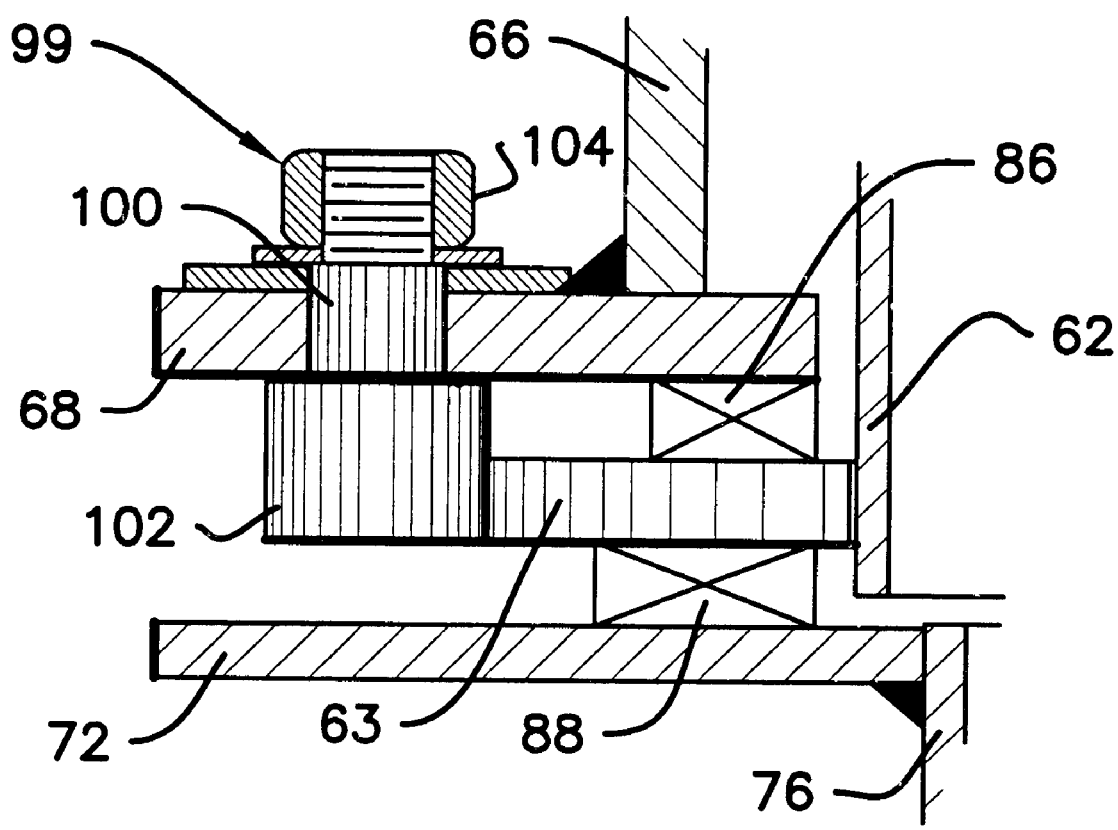
FIG. 7 is an enlarged, fragmentary, sectional view taken generally along line 7—7 in FIG. 6 showing the preferred idler bearing arrangement.
Figure 8:
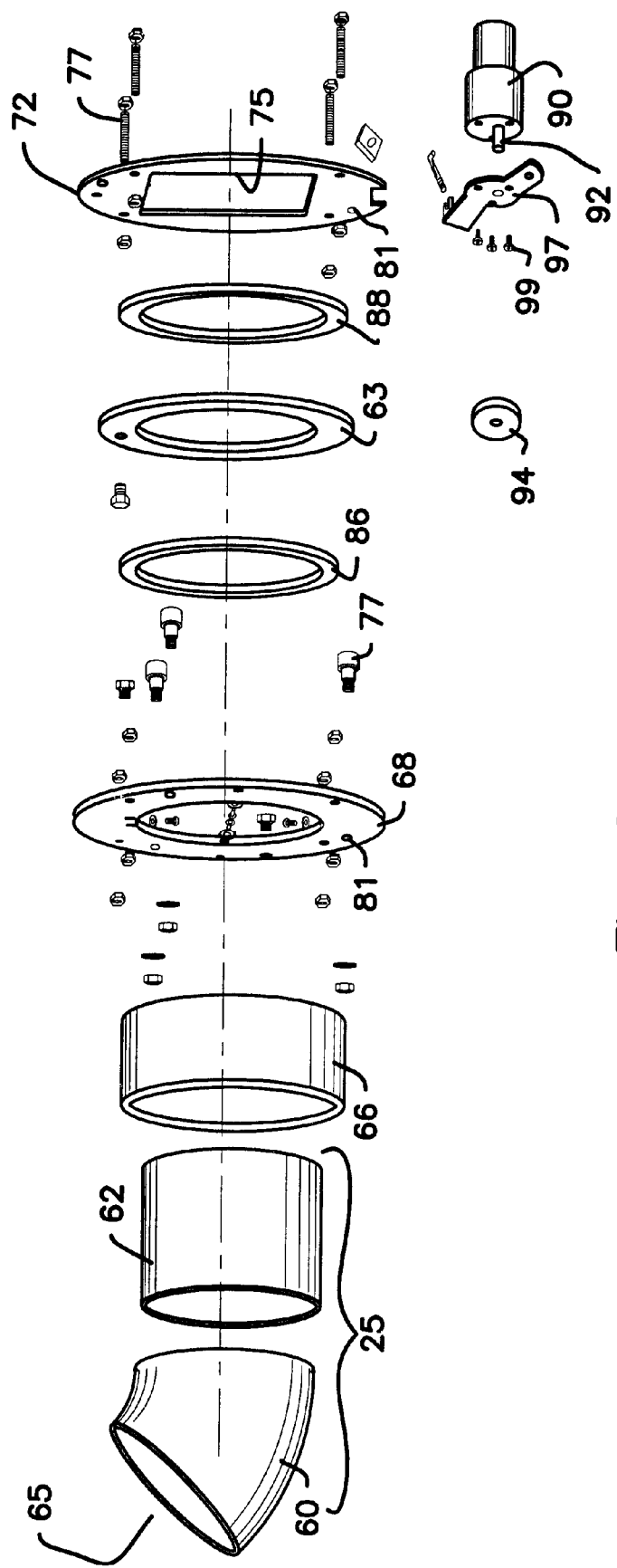
FIG. 8 is a partial, exploded isometric assembly view, with portions thereof broken away or omitted for brevity or shown in section for clarity.

It will be apparent that the friction ring 63 surrounding the external lower periphery of pipe 62 is positioned between plates 68 and 72 (FIGS. 4, 5). A pair of annular, ring shaped flexible bearings 86 and 88 contact the friction drive ring 63 on each side, sandwiching it between plates 68 and 72. As best seen in FIGS. 4, 6, and 8, a drive motor 90 comprising driveshaft 92, revolves a rubber covered friction wheel 94 that frictionally engages the friction drive ring 63 to turn pipe 62 and thus hood apparatus 25. Motor 90 is secured to plate 72 by a bracket 97 held by fasteners 99 FIG. 8). To maintain concentricity as the pipe 63 revolves, the friction ring 63 contacts a plurality of radially spaced-apart cam idler bearings 99 (FIG. 6). As best seen in FIG. 7, the idler bearings 99 comprise a threaded shaft 100 that mounts a roller 102. A fastener 104 secures the bearing stricture 99. Each roller 102 rotatably abuts the friction drive ring 63.

Figure 3:
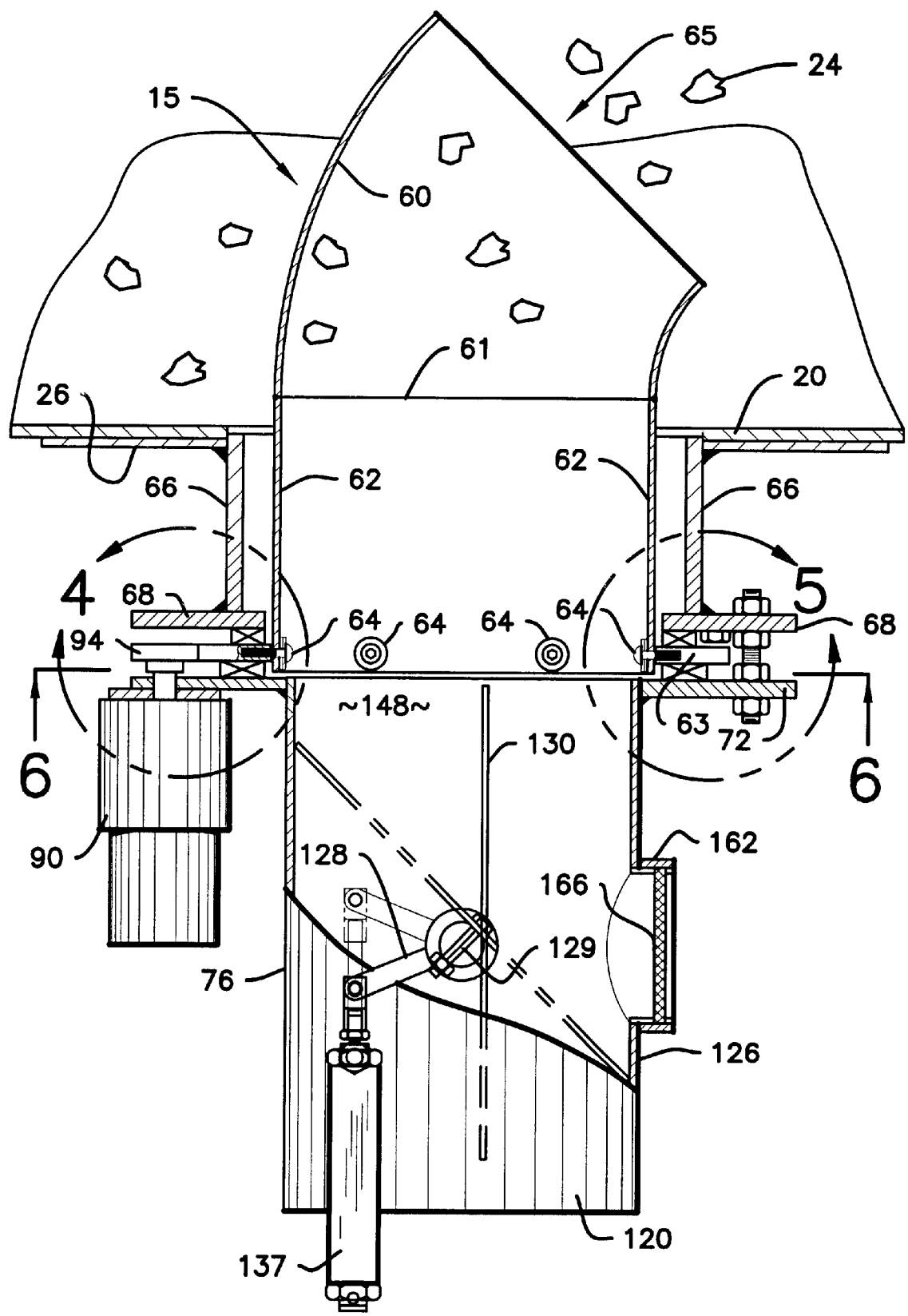
FIG. 3 is an enlarged, fragmentary, sectional view of the preferred sampling device, showing the head disposed in a particle discharge position, and showing the preferred internal butterfly valve open, with dashed lines indicating moved positions.
Figure 9:
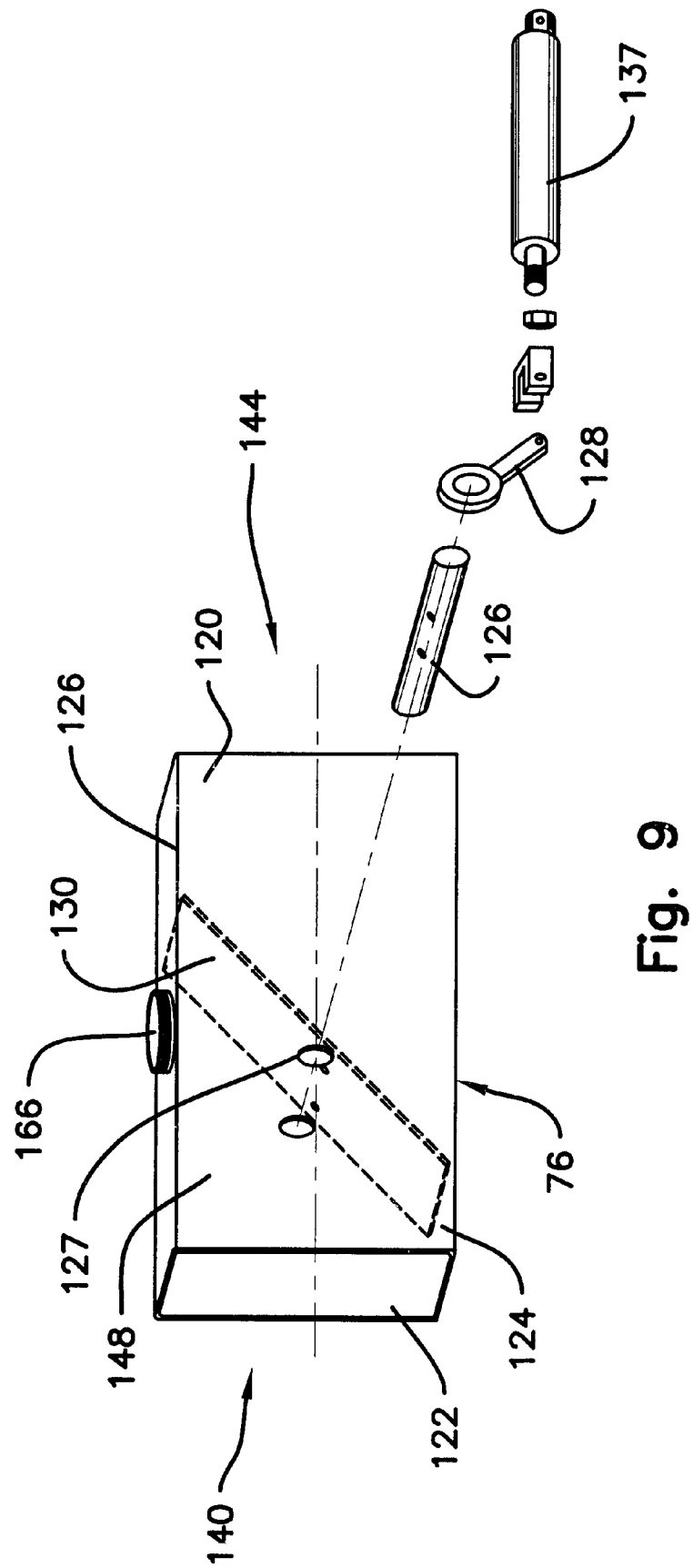
FIG. 9 is a partial, exploded isometric assembly view similar to FIG. 8, with portions thereof broken away or omitted for brevity or shown in section for clarity.

With primary reference now directed to FIGS. 3 and 9, the valve housing 76 is generally in the form of a parallelepiped. It is welded to plate 72 (FIG. 8) within the rectangular orifices 75 previously discussed. (For best viewing, FIGS. 8 and 9 should be positioned as in FIG. 10). It comprises an elongated tube 120 of generally rectangular cross section, comprising sides 122, 124 and a top 126 (FIG. 9) Orifices 117 in sides 122 and 124 are aligned with an internal axle 126 that controls and mounts a flat, rigid, valve plate 130. Lever 128 projecting from axle 126 is actuated by a conventional cylinder 137 to open or close valve plate 130 via bolt 129 (FIG. 3). The plate 130 is preferably the same width as the top 126 of box 120. When it lies diagonally as in FIG. 9, it occludes the air pathway between open box ends 140 and 144. Suitable electronic circuitry will control motor 90, to orient head 25 properly, and cylinder 137, to open or close valve box 6. When the box is "opened " by aligning plate 130 parallel with top 126 as in FIG. 2, air is suctioned through the box. The box ends are thus in fluid flow communication with the open end 65 (FIGS. 3, 8) of the hood assembly.

Importantly, a particle sampling region 148 (FIG. 9) is defined between the closed valve plate 130, the open box end 140 and top 126. As viewed in FIG. 3, this sampling region 148 has a triangular cross section. In the sampling mode (i.e., FIG. 1) particles (i.e., wood flake) entering hood apparatus 25 drop through the apparatus and reach sampling region 148. These particles impact valve plate 130 within box assembly 76. A collar 162 is formed in box top 126 (FIGS. 3, 9). This collar surrounds a high temperature, impact-resistant inspection window 166. As best seen in FIG. 2, the moisture reading apparatus 28 comprises a housing 170 connected to collar 162 by tube 169. A moisture sensor, preferably comprising a Moisture Systems Quad 8000 unit disposed within housing 170 periodically reads the moisture content of a sample within region 148 (FIG. 9). Light first directed through the inspection window is reflected back to the unit for obtaining a moisture reading used by the system, as explained hereinafter.

Operation

The apparatus is installed as in FIGS. 1 and 2. Starting from the position of FIG. 1, wood flakes enter the hood apparatus, passing through elbow 60 (FIG. 3) that is aimed upstream. At this time the hood apparatus 25 is appropriately aimed upstream by motor 90; concurrently cylinder 137 closes the valve plate 130. Particles pass through the interior of the apparatus, entering box 76 and sampling compartment 148. After a sample is obtained over a timed period, the hood can be rotated downstream. The hood apparatus 25 is rotated to face downstream stream by motor 90, assuming the position of FIG. 2.

The compartment 148 contains inspection window 166, through which the moisture sensor derives its readings. Accumulated particles are sensed within this chamber. Once a moisture reading is taken, Valve plate 130 is thereafter opened by cylinder 137. Air suctioned into box 76 through exposed orifice 144 (FIG. 9) vigorously transports the sample of flakes back through pipe 62 and elbow 60 into the airstream within conduit 20. In this manner each sample used to provide a moisture reading is returned to the manufacturing process, rather than being wasted. Once the "sampled" flakes are returned to the conduit 20, the process may repeat, The hood is rotated back into a position, as if FIG. 1, facing upstream, and the valve plate 130 is closed to seal the vacuum.

Figure 11:
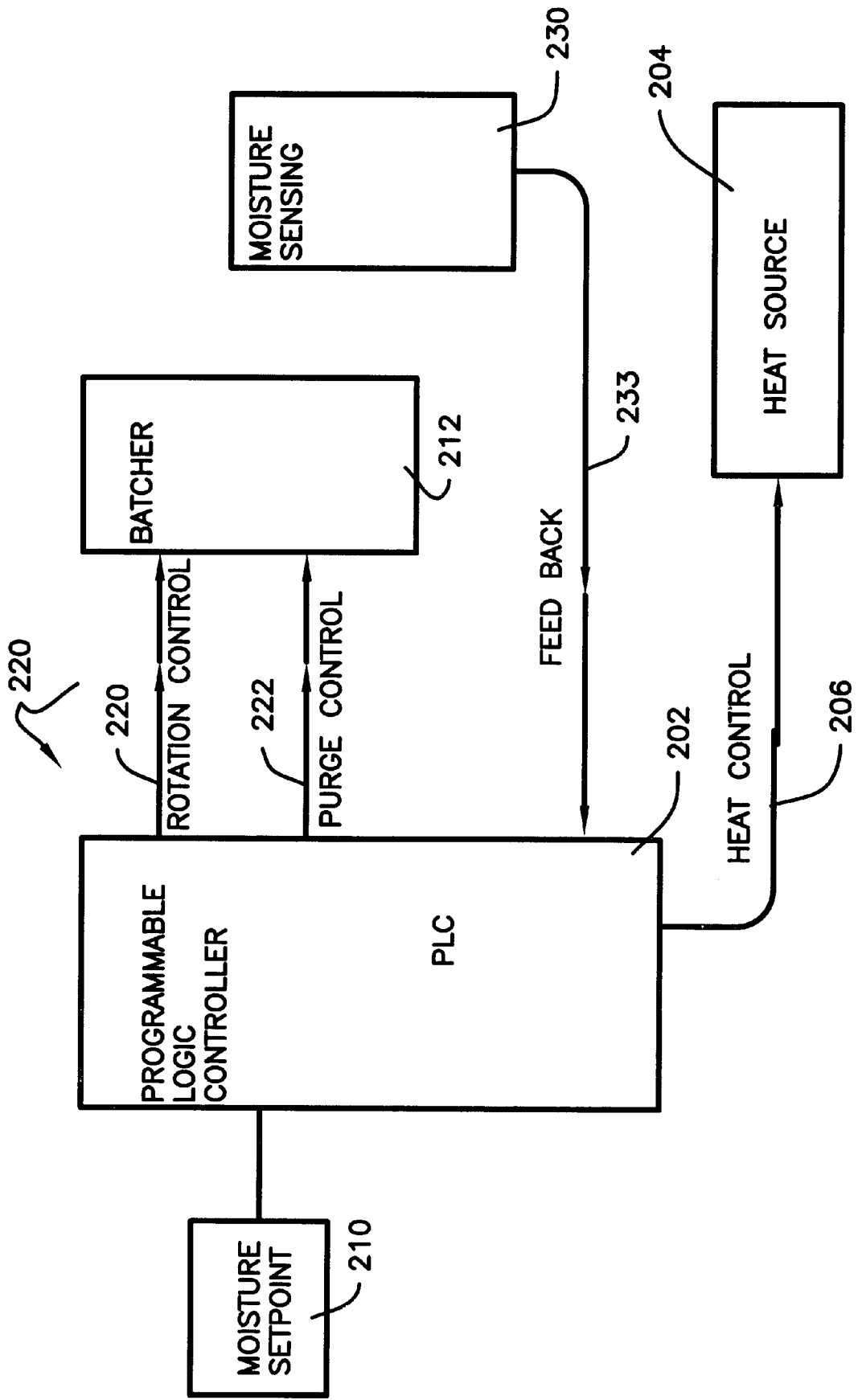

Turning to FIG. 11, the process is best understood by reference to preferred controller circuit 200. The programmable logic controller 202 ultimately controls the remote heat source 204 (i.e., within the remote, upstream heater that dries wood flakes 24 travelling through conduit 20). The moisture set point is determined by adjustment as indicated by block 210. The block 212 represents the mechanical aspects of the device; rotation of hood apparatus 25 is indicated by control line 220 and control of valve plate 130 is indicated by line 222. By adjusting the Moisture Systems Quad 8000 device discussed earlier, indicated by block 230 that communicates with PLC 202 via line 233, the desired dryness is established.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A device for sampling a stream of particulate material moving in a flow path through a tubular conduit, said device comprising:

hood means penetrating said conduit, the hood means comprising an open ended sample-intake spout and an opposite end in fluid flow communication through the device;

means for rotating said hood means between an upstream position with the spout facing the flow path to captivate samples and a downstream position for returning said samples into the flow path;

valve means for selectively closing said device when said hood means faces upstream and for venting said device when said hood means faces downstream;

valve housing means in fluid flow communication with said hood means for mounting said valve means;

means for selectively displacing said valve means between a closed position for obtaining said samples and an open position for returning the samples to the flow path within the conduit;

a sample collection compartment formed within said valve housing means by the closed valve means for temporarily holding samples of materials to be monitored;

moisture determining means for testing samples captivated within said collection compartment;

wherein said valve housing means comprises an inspection window adjacent said sample collection compartment, and said moisture determining means comprises means for reading sample moisture through said inspection window; and, circuit means for activating said means for rotating said hood means to rotate said hood means between operative positions and for opening said valve means so that samples that have been tested are returned via suction to the conduit flow path, and wherein, after tested samples have been returned to the conduit flow path, said circuit means closes said valve means and causes said means for rotating said hood means to return the hood means into a position to again take a sample so the sequence may repeat.

2. The device as defined in claim 1 wherein said hood means comprises:

an elbow with an open end forming a spout adapted to be directed upstream or downstream relative to the flow path within said conduit;

an elongated pipe connecting the elbow to the device; and, an annular friction drive ring coaxially mounted to the pipe.

3. The device as defined in claim 2 wherein said hood means pipe is concentrically surrounded by an external pipe extending from the conduit and terminating in an annular mounting flange spaced apart from said friction ring.

4. The device as defined in claim 3 wherein said valve housing means comprise an enclosure terminating in an annular, ring shaped mounting plate adapted to be fastened to said an annular mounting flange on said external pipe.

5. The device as defined in claim 4 wherein the friction drive ring is sandwiched between said external pipe flange and said ring shaped mounting plate.

6. The device as defined in claim 5 further comprising motor means for turning the hood means, said motor means comprising gear means for engaging the friction drive ring.

7. The device as defined in claim 5 further comprising annular, ring shaped flexible bearings on each side of the friction drive gear.

8. The device as defined in claim 5 further comprising a plurality of radially spaced-apart idler bearings that contact said friction drive ring to maintain hood means concentricity.

9. A moisture sampling device for sampling a stream of wood flakes moving in a flow path through a tubular conduit, said device comprising:

a rigid mounting flange adapted to be secured to the conduit for supporting the device;

a tubular hood extending through the conduit and into the flow path, the hood comprising a spaced apart spout comprising an open sample-intake end and an opposite, closed end;

means for rotating the hood for first positioning said spout into the flow path to captivate a sample, and to thereafter rotate the spout approximately 180 degrees to a downstream orientation;

a valve housing in fluid flow communication with said hood;

a valve disposed within said valve housing, the valve selectively displaceable between open and closed positions;

a sample collection compartment formed within said housing when said valve is closed for temporarily holding samples of materials to be monitored;

a sampling window formed in said housing adjacent said collection compartment; and, moisture determining means communicating through said window for testing samples captivated within said collection compartment.

10. The device as defined in claim 9 wherein said valve housing means comprises an inspection window adjacent said sample collection compartment, and said moisture determining means comprises optical means for reading sample moisture through said window.

11. The device as defined in claim 9 wherein said hood means comprises:

an elbow with an open end forming a spout adapted to be directed upstream or downstream relative to the flow path within said conduit;

an elongated pipe connecting the elbow to the device; and, an annular friction drive ring coaxially mounted to the pipe.

12. The defined in claim 11 wherein said valve housing means comprise an enclosure terminating in an annular, ring shaped mounting plate adapted to be fastened to said an annular mounting flange on said external pipe.

13. The device as defined in claim 12 further comprising motor means for turning the hood means, said motor means comprising gear means for engaging the friction drive ring.

14. The device as defined in claim 13 further comprising annular, ring shaped flexible bearings on each side of the friction drive gear.

15. The device as defined in claim 14 further comprising a plurality of radially spaced-apart idler bearings that contact said friction drive ring to maintain hood means concentricity.

16. The device as defined in claim 11 wherein the friction drive ring is sandwiched between said external pipe flange said ring shaped mounting plate.

* * * * *